US006617479B1

(12) United States Patent
Klausmeyer et al.

(10) Patent No.: US 6,617,479 B1
(45) Date of Patent: Sep. 9, 2003

(54) METHOD FOR PRODUCING ISOPROPYL CHLORIDE VIA LIQUID-PHASE HYDROCHLORINATION OF PROPYLENE

(75) Inventors: Rodney L. Klausmeyer, Wichita, KS (US); David E. Brummond, Cheney, KS (US)

(73) Assignee: Vulcan Chemicals division of Vulcan Materials Company, Birmingham, AL (US)

( * ) Notice: Subject to any disclaimer, the term of this patent is extended or adjusted under 35 U.S.C. 154(b) by 0 days.

(21) Appl. No.: 10/223,762

(22) Filed: Aug. 19, 2002

(51) Int. Cl.[7] .................. C07C 17/08; C07C 21/00; C07C 23/00; C07C 25/00
(52) U.S. Cl. ..................................... 570/250
(58) Field of Search ................ 570/246, 247, 570/248, 250

(56) References Cited

U.S. PATENT DOCUMENTS

| | | |
|---|---|---|
| 2,097,750 A | 11/1937 | Arnold et al. ............ 260/166 |
| 2,429,758 A | 10/1947 | Holmes ...................... 260/663 |
| 5,672,788 A | 9/1997 | Nappa et al. ............... 570/168 |

OTHER PUBLICATIONS

Stabo and Trabalka—Abstract of Romanian Patent No. 97443, Jul. 31, 1989.

Nakamato et al—Abstract of Japanese Patent No. 60178831, Sep. 12,1985.

*Primary Examiner*—Samuel Barts
*Assistant Examiner*—Elvis O. Price
(74) *Attorney, Agent, or Firm*—Armstrong, Westerman & Hattori, LLP

(57) ABSTRACT

Preparing isopropyl chloride (2-chloropropane) employing propylene, hydrochloric acid and ferric chloride catalyst in an isopropyl chloride solution at effective temperatures and pressure to produce 2-chloropropane. The amount of ferric chloride catalyst is less than that conventionally employed and the temperature and pressure are greater than conventionally employed.

12 Claims, No Drawings

METHOD FOR PRODUCING ISOPROPYL CHLORIDE VIA LIQUID-PHASE HYDROCHLORINATION OF PROPYLENE

FIELD OF THE INVENTION

The herein disclosed invention finds applicability in the field of chlorinated hydrocarbons preparation.

BACKGROUND OF THE INVENTION

The inventor is developing a manufacturing process to produce isopropyl chloride (IPC, or 2-chloropropane) via the addition of anhydrous HCl to propylene. It is known in the art that the hydrochlorination process can be carried out in either the gas or liquid phases.

Nappa et al (U.S. Pat. No. 5,672,788) teach a process for preparing difluoroethane by reacting HCl with chloroethylene to produce dichloroethane and converting this product to difluoroethane. The Nappa et al process is distinct from the herein disclosed invention in that the reaction conditions are distinct, the starting materials are different as are the reaction conditions.

Arnold and Lessig (U.S. Pat. No. 2,097,750) teach the preparation of alkyl chlorides in the vapor phase by passing HCl and an alkene over a halide of a Group IIB metal supported on activated carbon. Example five in their patent describes the formation of isopropyl chloride by passing HCl and propylene over a catalyst of zinc chloride on charcoal at atmospheric pressure and 150 degrees C.

Holmes (U.S. Pat. No. 2,429,758) teaches anhydrous calcium sulfate ("Drierite") to effect the reaction between HCl and propylene in the vapor phase. Temperatures and pressures ranged from 35 to 200 degrees C., zero to 100 psig.

Stabo and Trabalka, Romanian Patent RO 97443 (Jul. 31, 1989) describe the hydrochlorination of propylene, presumably in the liquid phase, between 0–120 degrees C. and 1–5 kgf/cm2 (0.3 to 1.7 psig) using aluminum chloride catalyst complexed with 1,1,1-trichloroethane, 1,1,2-trichloroethane, or 2-chloropropane.

Nakamoto et al, JP 60178831 (Sep. 12, 1985) reported a reaction using liquid isopropyl chloride as a solvent in the presence of a Friedel-Crafts catalyst, preferably ferric chloride. Preferred temperatures were <30 degrees C. with an HCl/propylene molar ratio of >1.05. Cited ferric chloride concentration was 1 gram per 100 ml solution.

None of the prior art patents teach the inventive process of the herein disclosed invention.

An in-house development of a liquid-phase process for the production of isopropyl chloride began in late 1998. Very quickly, the preferred method became hydrochlorination of propylene in liquid isopropyl chloride solvent using ferric chloride catalyst and high HCl/propylene feed ratios (1.5/1 to 2/1 molar). The excess HCl served as a stripping gas to remove the IPC product from the reactor as a vapor. Reaction pressures and temperatures were kept low, e.g., below 15 psig and 40 degrees C., to minimize side reactions between propylene and the catalyst. These side reactions were believed to increase catalyst consumption and cause the formation of 1,2-dichloropropane and heavier components. Minimum concentration of the ferric chloride catalyst necessary to initiate and sustain the reaction ranged from 1000–6000 ppm by weight, depending upon the purity of the IPC initially charged to the reactor. These temperature and pressure ranges were based upon the Nakamoto et al above cited and the inventors' own experience with its commercial operation to produce 1,1,1-trichloroethane by hydrochlorination of vinylidene chloride. The ferric chloride concentration was the minimum necessary to achieve a sustainable reaction.

OBJECTS OF THE INVENTION

A main object of this invention is for the efficient preparation of isopropyl chloride under conditions which preserve the catalyst.

A significant object of this invention is to produce isopropyl chloride under conditions which reduce by-product formation.

These and other objects of the present invention will become apparent from a reading of the following specification taken in conjunction with the enclosed examples.

SUMMARY OF THE INVENTION

In simplest terms the reaction of this invention is carried out by incorporating a ferric chloride catalyst ($FeCl_3$) in IPC(2-chloropropane) as the solvent and sparging a proper ratio of HCl and propylene (in their gaseous form) through the IPC solvent containing $FeCl_3$ catalyst. The HCl and propylene react to form IPC (isopropyl chloride). Some of the IPC is removed in vapor form from the reaction mixture by sparging with HCl. Most of the IPC is removed in the liquid phase. The preferred process is run on a continuous basis.

A process for the production of isopropyl chloride (IPC) via the ferric chloride-catalyzed liquid-phase hydrochlorination of propylene is described herein in detail. The improvement consists of operating the reactor at higher temperatures and pressures than those described in prior art preferred embodiments. This allows the concentration of ferric chloride catalyst to be reduced by at least a factor of ten, which improves catalyst life, lowers by-product formation, and reduces the amount of waste for disposal.

The method of this invention is designed to reduce the amount of ferric chloride necessary to catalyze the production of isopropyl chloride via liquid-phase hydrochlorination of propylene in isopropyl chloride solvent. The inventive process consists of operating the reaction at a higher temperature and pressure, which surprisingly reduces the concentration of catalyst needed, extends catalyst-life, and greatly reduces the formation of by-products via reaction of the catalyst with the solvent. The process also allows for the use of HCl/propylene molar feed ratios of approximately 1.0–1.2 without any significant loss in feed conversions. This reduces the amount of unreacted gas that must be recycled, thereby reducing the size of, or eliminating, a recycle compressor and associated equipment.

The process of the invention is for the production of isopropyl chloride via the liquid-phase hydrochlorination of propylene in isopropyl chloride solvent. The improvement consists in operating the reactor at a temperature of at least 50 degrees C. or higher and at a pressure of 30 psig or higher. Molar HCl to propylene feed ratio of 1.0 to 1.2 is used. Under these conditions, rapid reaction rates and greater than 90 percent feed conversions can be achieved using ferric chloride catalyst concentrations in the liquid solvent of 15–250 ppm by weight. These low catalyst concentrations greatly reduce side reactions between the ferric chloride and the solvent or feed materials. At higher catalyst concentrations, these side reactions cause the reactor solution to darken and develop a precipitate. At the claimed lower catalyst concentrations little or no solution darkening or solids formation occurs. Product isopropyl chloride can be removed from the reactor as a vapor, a liquid, or a combination of the two.

This contrasts with the prior art process which operated at 30 degrees C. or lower and at a total system pressure of 20 psig or less. Molar HCl to propylene feed ratios of 1.5 to 2.0 were used. To maintain rapid reaction rates and greater than 90 percent propylene conversion, ferric chloride catalyst concentrations in the liquid of 1000–6000 ppm by weight were required. The desired isopropyl chloride product was removed solely as a vapor using the unreacted HCl as a stripping gas.

Exemplary effective amounts for carrying out the process of this invention are here set forth and elsewhere in this specification, ferric chloride catalyst in an amount of about 15–350 ppm based on the initial amount of isopropyl chloride. A preferred range of ferric chloride is 50 to 100 ppm and a most preferred amount is 100 ppm. If less than 15 ppm of $FeCl_3$ is used, the reaction slows to unacceptable levels. The volume of IPC employed is in the range of 500–700 cc. However, this volume varies as the reaction is taking place. The ratio of HCl/propylene feed ranges in moles/hour of 0.75 HCl to 0.75 propylene; a range of 1.50 HCl to 0.75 propylene; and the preferred range of 0.825 HCl to 0.75 propylene. The temperature can be the range of 50° C. to 80° C. with 70° C. being preferred. The pressure can be 30 to 100 psig or higher with 40 psig being preferred. In the laboratory the experiments can be carried out in a liter vessel. Commercially, the process can be carried out in a 500 gallon vessel, the size of the vessel is not critical. Throughout the disclosure the amounts set forth are proximate and can be varied by those skilled in the art without violating the spirit of this invention.

EXAMPLES

Tests were conducted in a 1-liter Pyrex pressure reactor from Ace Glass Incorporated, rated to 45 psig at 100 degrees C. Vapor HCl and propylene feeds were continuously metered into the reactor using thermal Mass Flow Controllers and introduced below the liquid surface through a fritted glass sparger. Liquid volume in the reactor was typically between 400 and 800 cc. Reactor contents were continuously stirred during operation using a glass and Teflon paddle-type stirrer. Temperature was maintained by immersing the entire reactor in a thermostatically controlled water bath. A Teflon valve/dip tube assembly provided a means of removing the reactor liquid continuously or batchwise. A vapor line on the top of the reactor allowed vapor isopropyl chloride, HCl, and propylene to be removed continuously. This line was equipped with a pressure control assembly that allowed the system pressure to be varied as desired. The vent was equipped with an on-line gas chromatograph for quantitation of unreacted propylene, from which propylene conversion and isopropyl chloride production were calculated.

Reactor solutions were made by pouring a weighed amount of IPC into the reactor, usually 400–500 grams, then adding a pre-weighed amount of dry ferric chloride through a port on top of the reactor. A small flow of dry nitrogen was continually passed through the vapor space of the reactor during the charging process to help exclude atmospheric moisture. The catalyst addition port was quickly sealed, and the HCl and propylene feeds started within five minutes of adding the ferric chloride. Temperature and pressure were then established for the experiment at hand. The system was operated for at least an hour before sampling to allow equilibrium to be established.

Example 1

In Example 1, 0.27 gram of ferric chloride was added to 400 grams of fresh isopropyl chloride in the reactor to give a starting concentration of 675 ppm by weight. The HCl/propylene molar feed ratio was 1.75, temperature 25–30 degrees C., pressure 10–15 psig. Propylene conversion after one hour of run time was only 31 percent. Halving the feed rates between samples 1 and 2 offered little improvement, as conversions continued to decline to 17 and 13 percent at 1.9 and 2.2 hours, respectively. This example illustrated that 675 ppm $FeCl_3$ was insufficient to catalyze the reaction of even 0.75 moles/hr of propylene at these conditions.

| Example 1-0.27 gram FeCl3, ~675 ppm. Vapor Product Removal | | | |
|---|---|---|---|
| Sample Number | 1 | 2 | 3 |
| Elapsed Time, hours | 1.0 | 1.9 | 2.2 |
| Temperature, C | 25 | 30 | 31 |
| Pressure, psig | 10.5 | 15 | 17 |
| Feed mole/hr | | | |
| HCl | 2.63 | 1.32 | 1.32 |
| C3H6 | 1.50 | .75 | .75 |
| HCl/C3H6 (molar) | 1.75 | 1.76 | 1.76 |
| C3H6 Conv, % | 31.0 | 17.1 | 13.5 |
| (g C3H6 fed)/(g FeCl3 charged) | 238 | 386 | 423 |

Example 2

In Example 2, 0.50 gram of ferric chloride was added to 500 grams of fresh isopropyl chloride in the reactor to give a starting concentration of ~1000 ppm by weight. The HCl/propylene feed ratio was 2.0, temperature 31–32 degrees C., pressure 9 psig. Propylene conversion remained above 98 percent for nearly 6.2 hours, dropping to 94.6 percent in Sample number 7 at 6.7 hours. This example illustrated that 1000 ppm $FeCl_3$ was sufficient to catalyze the reaction of at least 0.75 moles per hour of propylene with at least 98 percent conversion for over six hours. Expressed another way, about 390 grams of propylene were converted at greater than 98 percent efficiency per gram of ferric chloride charged. The isopropyl chloride formed was removed from the reactor as a vapor using the excess HCl as a stripping gas. By the end of the experimental series, the reactor solution had turned from the initial clear yellow-brown color to black. A gray-colored precipitate was also visible in the liquid.

| Example 2-0.50 gram FeCl3, ~1000 ppm. Vapor Product Removal | | | | |
|---|---|---|---|---|
| Sample Number | 4 | 5 | 6 | 7 |
| Elapsed Time, hours | 0.9 | 5.0 | 6.2 | 6.7 |
| Temperature, C | 31 | 32 | 31 | 31 |
| Pressure, psig | 9 | 9 | 9 | 9 |
| Feed mole/hr | | | | |
| HCl | 1.50 | 1.50 | 1.50 | 1.50 |
| C3H6 | 0.75 | 0.75 | 0.75 | 0.75 |
| HCl/C3H6 (molar) | 2.0 | 2.0 | 2.0 | 2.0 |
| C3H6 Conv, % | 99.8 | 99.7 | 97.9 | 94.6 |
| (g C3H6 fed)/(g FeCl3 charged) | 56 | 310 | 390 | 422 |

Example 3

The conditions of Example 2 were essentially repeated, except that the HCl feed rate was reduced to 0.90 moles per hour to give an HCl to propylene feed ratio of 1.20. Reactor pressure was slightly higher at 11 instead of 9 psig, initial ferric chloride concentration was ~1400 ppm by weight (0.57 gram). Propylene conversion dropped below 98 percent after between 1.7 and 2.2 hours of operation, reaching 58 percent at 3.2 hours in Sample number 11. This example illustrated that at these conditions, reducing the HCl to propylene feed ratio had a detrimental effect on catalyst life. Only slightly more than 72 grams of propylene were converted at greater than 98 percent efficiency per gram of ferric chloride charged. The isopropyl chloride formed was removed from the reactor as a vapor. By the end of the experimental series, the reactor solution had turned from the initial clear yellow-brown color to black. A gray-colored precipitate was also visible in the liquid.

Example 3-0.57 gram FeCl3, ~1400 ppm. Vapor Product Removal

| Sample Number | 8 | 9 | 10 | 11 |
|---|---|---|---|---|
| Elapsed Time, hours | 0.9 | 1.7 | 2.2 | 3.2 |
| Temperature, C | 32 | 32 | 32 | 29 |
| Pressure, psig | 11 | 11 | 11 | 11 |
| Feed mole/hr | | | | |
| HCl | 0.90 | 0.90 | 0.90 | 0.90 |
| C3H6 | 0.75 | 0.75 | 0.75 | 0.75 |
| HCl/C3H6 (molar) | 1.20 | 1.20 | 1.20 | 1.20 |
| C3H6 Conv, % | 99.4 | 98.4 | 96.5 | 58.6 |
| (g C3H6 fed)/(g FeCl3 charged) | 49 | 72 | 120 | 175 |

Example 4

In Example 4, 0.51 gram of ferric chloride was added to 500 grams of fresh isopropyl chloride in the reactor to give a starting concentration of ~1000 ppm by weight. The HCl/propylene feed ratio was 1.50, temperature 60–61 degrees C., pressure 30 psig. Propylene conversion remained above 98 percent for the duration of this test, in excess of 22 hours. This illustrated that at these elevated temperature and pressure conditions relative to those in Example 2, 1000 ppm FeCl$_3$ was sufficient to catalyze the reaction of at least 0.75 moles per hour of propylene with at least 98 percent conversion for more than 22 hours. This was in spite of the potentially detrimental effect of a lower HCl/propylene feed ratio as demonstrated in Example 3. Expressed another way, over 1387 grams of propylene were converted with greater than 98 percent efficiency per gram of ferric chloride charged. The isopropyl chloride formed was removed from the reactor as a vapor. By the end of the experimental series, the reactor solution had turned from the initial clear yellow-brown color to black. A gray-colored precipitate was also visible in the liquid.

Example 4-0.51 gram FeCl3, ~1000 ppm. Vapor Product Removal

| Sample Number | 12 | 13 | 14 | 15 |
|---|---|---|---|---|
| Elapsed Time, hours | 1.2 | 10.1 | 16.4 | 22.4 |
| Temperature, C | 60 | 61 | 61 | 61 |
| Pressure, psig | 30 | 30 | 30 | 30 |
| Feed mole/hr | | | | |
| HCl | 1.13 | 1.13 | 1.13 | 1.13 |
| C3H6 | 0.75 | 0.75 | 0.75 | 0.75 |
| HCl/C3H6 (molar) | 1.50 | 1.50 | 1.50 | 1.50 |
| C3H6 Conv, % | 99.7 | 99.5 | 99.4 | 98.9 |
| (g C3H6 fed)/(g FeCl3 charged) | 76 | 625 | 1015 | 1387 |

Example 5

In Example 5, 0.06 gram of ferric chloride was added to 500 grams of fresh isopropyl chloride in the reactor to give a starting concentration of ~120 ppm by weight. The HCl/propylene feed ratio was 1.50, temperature 67–69 degrees C., pressure 40 psig. Propylene conversion remained above 98 percent for the duration of this test, in excess of 16 hours. This illustrated that at these elevated temperature and pressure conditions relative to those in Example 2, 120 ppm FeCl$_3$ was sufficient to catalyze the reaction of at least 0.75 moles per hour of propylene with at least 98 percent conversion for over 16 hours. In addition, Sample number 19 was taken with the feed rates doubled. Propylene conversion was essentially unchanged from the previous sample at half the rates. This illustrated that the 120 ppm FeCl3 was sufficient to catalyze the reaction of at least 1.5 moles per hour of propylene with greater than 98 percent conversion. Expressed another way, over 10,000 grams of propylene were converted with greater than 98 percent efficiency per gram of ferric chloride charged. The isopropyl chloride formed was removed from the reactor as a vapor. By the end of the experimental series the reactor solution had not changed in appearance from the initial clear, very light yellow color. No visible precipitate was present. This illustrated that the side reactions causing the solution to darken and the precipitate to form were minimized or eliminated by going to the high temperature/pressure, low ferric chloride conditions.

Example 5-0.06 gram FeCl3, ~120 ppm. Vapor Product Removal

| Sample Number | 16 | 17 | 18 | 19 |
|---|---|---|---|---|
| Elapsed Time, hours | 2.3 | 8.7 | 13.6 | 16.4 |
| Temperature, C | 67 | 68 | 69 | 67 |
| Pressure, psig | 40 | 40 | 40 | 42 |
| Feed mole/hr | | | | |
| HCl | 1.13 | 1.13 | 1.13 | 2.25 |
| C3H6 | 0.75 | 0.75 | 0.75 | 1.50 |
| HCl/C3H6 (molar) | 1.50 | 1.50 | 1.50 | 1.50 |
| C3H6 Conv, % | 99.2 | 99.3 | 99.0 | 98.9 |
| (g C3H6 fed)/(g FeCl3 charged) | 1227 | 4567 | 8038 | 10063 |

Example 6

The test series begun in Example 5 was continued with the same solution and conditions, but the HCl feed rate was reduced to 0.83 moles per hour to give an HCl/propylene feed ratio of 1.10. The elapsed times shown for Example 6 are thus cumulative since they include the times from Example 5 as well. The isopropyl chloride formed was removed both continuously as a vapor and periodically as a liquid drained from the reactor. Ferric chloride was thus also gradually removed from the system as the reactor was drained. For this reason, analyzed values for the ferric chloride concentration in the reactor liquid are also shown in the table for Example 6. Propylene conversion was over 99 percent at 21.6 hours, Sample 21. Over 12,800 grams of propylene had thus been processed per gram of ferric chloride with over 99 percent efficiency. Stated another way, over 99 percent propylene conversion was maintained for another 5.2 hours since the conclusion of Example 5, despite the low HCl/propylene ratio and the gradual removal of ferric chloride from the system. Analysis of the reactor liquid in Sample 21 showed 17 ppm $FeCl_3$.

Propylene conversion dropped in Sample 22 to 91 percent, with analyzed ferric chloride concentration 15 ppm. An additional 0.03 gram of ferric chloride was added after Sample 21. Sample 22 at 29 hours showed 99.9 percent propylene conversion, 38 ppm dissolved ferric chloride. Sample 24 at 38.4 hours showed 99.0 percent propylene conversion, 32 ppm dissolved ferric chloride. In excess of 15,000 grams of propylene per gram of total ferric chloride added had been processed during the tests of Examples 5 and 6. By the end of the experimental series the reactor solution had not changed in appearance from the initial clear, very light yellow color. No visible precipitate was present. Example 6 illustrates the benefit of higher temperature and pressure allowing near stoichiometric HCl/propylene feed ratios, low ferric chloride concentrations, and greatly reduced undesirable side reactions.

Advantages of the Process
 a. Minimization or elimination of unwanted side reactions,
 b. Reduction of the amount of used, inactive catalyst for disposal,
 c. Cost reduction owing to the greatly improved yield of isopropyl chloride per unit weight of ferric chloride catalyst,
 d. The flexibility to design a system using vapor product removal, liquid product removal, or a combination of both.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A method for the production of isopropyl chloride comprising reacting effective amounts of hydrochloric acid and propylene in a isopropyl chloride solvent containing ferric chloride at a temperature of greater than 50° C. and a pressure greater than 30 psig.

2. The method of claim 1 wherein the effective amounts, in moles per hour, of hydrochloric acid and propylene are 0.75 hydrochloric acid to 0.75 propylene.

3. The method of claim 1 wherein the effective amounts, in moles per hour, of hydrochloric acid and propylene are 0.825 hydrochloric acid to 0.75 propylene.

4. The method of claim 1 wherein the effective amounts, in moles per hour, of hydrochloric acid and propylene are 1.50 hydrochloric acid to 0.75 propylene.

5. The method of claim 1 wherein the pressure is greater than 40 psig.

6. The method of claim 1 wherein the amount of ferric chloride is 100 ppm.

7. A method for the production of isopropyl chloride by liquid-phase hydrochlorination comprising reacting effective amounts of propylene and hydrochloric acid in the presence of 10 to 350 ppm ferric chloride catalyst in a reactor solution at an operating temperature of 50–80° C. and at a pressure greater than 30 psig.

8. The method of claim 7 wherein the operating temperature is at least 50° C.

9. The method of claim 8 wherein the temperature is 70° C.

10. The process of claim 7 wherein the isopropyl chloride is removed by sparging with HCl.

11. A method for the production of isopropyl chloride comprising reacting HCl and propylene in the presence of 15–300 ppm of ferric chloride in an isopropyl chloride solvent at a temperature in the range of 50° C. to 80° C. and at a pressure of 30 to 100 psig or higher.

12. The process of claim 11 wherein the ferric chloride is in an amount of 50 to 100 ppm, the temperature is about 60° to 70° C. and the pressure is about 30° psig.

| Example 6-Continuation of Example 5, Liquid and Vapor Product Removal | | | | | |
|---|---|---|---|---|---|
| Sample Number | 20 | 21 | 22 | 23 | 24 |
| Elapsed Time, hours | 17.6 | 21.6 | 25.1 | 29.0 | 38.4 |
| Temperature, C | 69 | 69 | 67 | 69 | 70 |
| Pressure, psig | 42 | 42 | 42 | 42 | 42 |
| Feed mole/hr | | | | | |
| HCl | 0.83 | 0.83 | 0.83 | 0.83 | 0.83 |
| C3H6 | 0.75 | 0.75 | 0.75 | 0.75 | 0.75 |
| HCl/C3H6 (molar) | 1.10 | 1.10 | 1.10 | 1.10 | 1.10 |
| C3H6 Conv, % | 99.8 | 99.4 | 91.0 | 99.9 | 99.0 |
| (g C3H6 fed)/(total g FeCl3 charged) | 10703 | 12800 | 14685 | 12122 | 15307 |
| Analyzed ppm FeCl3 in Liquid | 23 | 17 | 15 | 38 | 32 |
| | | | | Additional 0.03 gram FeCl3 added Between Sample Numbers 22 & 23 | |